United States Patent [19]

Wolf et al.

[11] 4,320,109

[45] Mar. 16, 1982

[54] IMMUNORADIOMETRIC ASSAY EMPLOYING TERMINAL RADIONUCLIDE LABELING AND SYNTHESIS OF CONJUGATES FOR SUCH ASSAY

[75] Inventors: Walter Wolf, Northridge; Robert M. Nakamura, Rolling Hills, both of Calif.; Ata Gokce, Istanbul, Turkey; Manuel Tubis, Laguna Hills; Timothy J. O'Brien, Pasadena, both of Calif.

[73] Assignee: The University of Southern California, Los Angeles, Calif.

[21] Appl. No.: 53,472

[22] Filed: Jun. 29, 1979

[51] Int. Cl.[3] ............... G01N 33/48; G01N 33/56; A61K 43/00
[52] U.S. Cl. ............................ 424/1; 23/230 B; 424/12
[58] Field of Search ............... 424/1, 1.5, 12; 23/230 B

[56] References Cited

U.S. PATENT DOCUMENTS

| | | | |
|---|---|---|---|
| 4,034,074 | 7/1977 | Miles | 424/1 |
| 4,041,146 | 8/1977 | Giaever | 424/1 |
| 4,166,844 | 9/1979 | Tu | 424/1 |

Primary Examiner—Christine M. Nucker
Attorney, Agent, or Firm—Nilsson, Robbins, Dalgarn, Berliner, Carson & Wurst

[57] ABSTRACT

An immunoradiometric assay in which an antigen is reacted to its specific antibody, which complex is then separated and further reacted with a second, universal antibody. This second, universal antibody contains a chelating moiety, such as transferrin, capable of binding specifically and strongly short-lived radionuclides. The second complex, once formed is reacted with a radionuclide and the radio-activity is measured, determining thereby the quantity of the unknown antigen originally present.

21 Claims, 1 Drawing Figure

IMMUNORADIOMETRIC ASSAY EMPLOYING TERMINAL RADIONUCLIDE LABELING AND SYNTHESIS OF CONJUGATES FOR SUCH ASSAY

BACKGROUND AND SUMMARY OF THE INVENTION

Radioimmunoassay (RIA) and related techniques are based on the principle that a substance such as an antigen, present in, e.g., a biological sample can react specifically and uniquely with another substance, such as an antibody, to form a complex that can readily be separated from either of the parent compounds. Present radioimmunoassay and related techniques all require that either the specific antibodies or the antigens be labelled with a radioactive agent usually I-125. Such labeling process may induce chemical and immunological changes, and because I-125 has a half-life of 60 days, also limits the shelf-life of the labeled product. The present invention provides a method that eliminates or minimizes the major problems of current radioactive usage. These problems are: (a) degradation of the antibody or antigen upon labeling; (b) limitation of the shelf life; and (c) radioactive waste generation. The present invention virtually eliminates the problems of radioactive waste created by the usage of the current radiolabeled materials. This invention does however retain and enhance the advantageous features of radionuclide usage.

Immunoassays require an antigen-antibody reaction, followed by a separation of the bound antigen-antibody complex from the unreacted reagent. The general method in use utilizes a second precipitating antibody, generated against the first antibody. The first antibody is used to neutralize (i.e., react to form antigen-antibody complex) the antigen. Either of these antibodies are generally produced in a rabbit or a similar animal (guinea pig, goat, sheep, etc.). Using the rabbit as an example, the first antibody produced in the rabbit is an antigen in the system of another animal, e.g., goat. Thus, when the immunoglobulin, the class of proteins which form the antibody, is injected into a goat under the proper protocol for antibody production, the immune system of the goat will consider the rabbit immuno-globin as an antigen. The new (second) antibody produced by the goat to the rabbit immunoglobin will react with the rabbit (first) antibody. This reaction with the rabbit immunoglobin of antibody makes the goat antibody a universal reagent for the reaction because while the first antibody is specific and selective for a given antigen, the second antibody recognizes the "back" part of the first antibody, which is general.

The present invention identifies a specific reaction which will allow the analyst to utilize effectively and very efficiently a specially prepared second antibody as a universal reagent. This expedient utilizes coupling of a metal binding moiety or compound such as the chelating protein, e.g., transferrin, desferoxamine, D-penicillamine or the like to the non-reactive portion of the second antibody. After the initial antigen-antibody reaction, the resultant complex is separated from excess antibody and the complex is then reacted with the second antibody that has been modified by attachment of the metal binding component. Following this step, a short-lived radionuclide, such as In-113m, is added to the bound fraction. The transferrin moiety will bind this radioactive metal with a high affinity.

The radioindium is prepared by known techniques using a generator. The half-life of this isotope is so short (100 min.) that within two days (14 half-lives) the amount of radioactivity remaining is almost nil (0.005%). However, the life of this isotope is sufficiently long so that prompt measurement of the radioactivity will enable the analyst to obtain accurate results. Other short-lived radionuclides, arbitrarily defined here to have half-lives of on the order of less than or equal to 24 hours, are also suitable.

Thus, features of the present invention include (a) the use of a short lived radioactive nuclide which enhances and increases the sensitivity of detection of substances and eliminates problems of waste disposal; (b) the use of a terminal labeling procedure which eliminates the limited shelf-life of radioimmunoassay reagents; (c) the avoidance of iodination which eliminates the chemical degradation of the antigen or antibody to be labeled; and (d) the use of a terminally labelled, "universal reagent" which markedly decreases the cost of analysis.

Immunoradiometric assay (IRMA) to determine the amount of specific antigen in a sample containing an unknown amount of the antigen is, of course, known, for example as described by Miles, *Properties, Variants and Applications of the Immunoradiometric Method*, La Ricerca in Clinica e in Labortorio, Vol. V. p. 59 (1975), the disclosure of which is hereby incorporated by reference. The Miles technique generally consists of reacting the unknown amount of an antigen with a soluble antibody specific to the antigen and also tagged with a radionuclide, usually I-125. Enough of the tagged soluble antibody is added to react with all of the unknown amount of the antigen being measured. Unused tagged, soluble antibody is removed by reacting it with solid-phase antigen. The amount of radioactivity remaining in the solution is a measure of the unknown amount of the antigen being measured.

An alternative IRMA method involves the preliminary insolubilization of an unknown amount of an antigen being measured and then reaction with a soluble radioactively labeled antibody. The labeled complex is thus insoluble and the unreacted labeled antibody is washed away leaving the labeled complex, with the measure of radioactivity in this solid phase complex being a measure of the amount of antigen being measured. Various methods exist for insolubilization of the antigen for purposes of carrying out this alternate IRMA method, including reaction with solid phase antibody to form an antigen-immuno-adsorbent complex (AG-ImAd), also known as, "2-site IRMA". This, however, is restricted to antigens which can either bind simultaneously to at least two antibodies or bind to the labeled antibody after the non-immunological insolubilization procedure. The technique also requires an immunoadsorbent containing highly purified antigens for preparation of the labeled antibodies.

The Miles procedure for labeling an antibody for use in an IRMA or RIA process is complicated, expensive and because of the use of I-125 has the detrimental effects initially referred to above, i.e., the possibility of altering the immunological reactivity of the labeled antibody. Further, with radionuclides such as I-125, having long half-lives, there exists a radioactive waste problem. Further, the labeled antibody used in the procedure must be highly purified to make the procedure specific to the antigen of unknown amount being measured. This is costly and requires either storage of numerous specific radioactively tagged antibodies or tagging of a specific purified antibody with a radionuclide immediately prior to the IRMA procedure. Thus, there are problems of limited shelf life in the former case and of radioactive materials controls and waste in the latter case. For highly accurate results, Miles suggests an additional refinement of the IRMA procedure in which the labeled antibody is univalent, such as produced by papain digestion, thereby adding to processing costs. Identical problems exist in the alternative 2-site IRMA procedure. In addition, further purified antibody may be necessary to form the solid phase antibody.

Miles, supra describes the adaption of both IRMA and 2-site IRMA to the use of labeled antibody (e.g., I-125-anti-IgG) as an additional "universal reagent", thereby avoiding the necessity for the preparation of radioactive antibodies specific for the unknown antigen. For example in tagging the 2-site IRMA with I-125 anti-(IgG) "universal reagent," an unknown amount of antigen, e.g., human ferritin [h(ferritin)] is reacted with solid-phase antibody, e.g., guinea-pig-anti-(ferritin) [GP-anti-(ferritin)] resulting in an insolubilized GP-anti-(ferritin)-h(ferritin) complex. The complex is then reacted with a purified specific non-radioactive antibody from a different species, e.g., Rabbit-anti-(ferritin) [R-anti-(ferritin)] resulting in an insolubilized GP-anti-(ferritin)-h(ferritin)-R-anti-(ferritin) complex. A radioactively tagged antibody of the same species as the solid-phase antibody, e.g., I-125-GP-anti(R-IgG) is then reacted with insolubilized GP-anti-(ferritin)-h(ferritin)-R-anti-ferritin), with the measure of radioactivity present on the solid-phase, once separated out, being a measure of the unknown amount of the antigen being measured.

Miles' "universal reagent", I-125-GP-anti-(R-IgG), is extremely costly to make since up to 80% of the purified GP-anti-(R-IgG) is lost during the iodination procedure. Also this reagent has a limited shelf life and the use of this reagent, as well as any others tagged with heavy metal radionuclides having long half-lives, creates significant radioactive waste disposal problems.

It has also been suggested to tag antibodies for the assay of antigen levels with radionuclides having short half-lives and susceptible of chelating with an antibody-chelate conjugate. See, Pritchard Ackerman, Tubis and Blahd, *Indium-111-Labelled Antibody Heavy Metal Chelate Conjugates: A Potential Alternative to Radioiodination*, Proceedings of the Society for Experimental Biology and Medicine, Vol. 151, p. 297 (1976), the disclosure of which is hereby incorporated by reference. This reference describes the possibility of conjugating the IgG molecule to compounds, e.g., transferrin, D-penicillamine and desferoxamine containing free amino groups capable of chelating heavy metal ions and binding a radionuclide, e.g., Indium-111 or iron-59 to the IgG-chelate conjugate for tagging without significantly altering the immunoreactions of the IgG-chelate conjugate.

The Pritchard, et al conjugation procedure utilizes glutaraldehyde with its two active sites to couple the free amino groups on both the chelating and the IgG molecules. Lyophilized IgG is reconstituted in physiological buffered saline (PBS) and transferrin, D-penicillamine or desferoxamine are each reconstituted in PBS. The conjugation is performed by mixing IgG, chelating compound (transferrin, D-penicillamine or desferoxamine) and glutaraldehyde in specified amounts and dialyzing to remove the unreacted glutaraldehyde and centrifuging to remove any precipitate. The In-111-IgG-chelate conjugate is then synthesized using In-111-chloride. Binding of the In-111 by the chelate portion of the IgG-chelate conjugate is described as almost instantaneous.

Pritchard, et al's proposed IgG-chelate conjugate labeling is described as overcoming some objections to the use of radioiodine; the conjugation procedure is relatively simple, the labeled conjugate is pre-prepared, the basic reagents can be incorporated in "kit" form widely useable in nuclear medicine and radioassay laboratories, and the labeling with a radionuclide, e.g., In-111 can be carried out simply and instantaneously whenever needed.

However, there are several problems existing in this prior art, Miles' disclosure of a "universal" reagent In-125-GP-anti-(R-IgG) is universal only in the sense that only one labeled antibody I-125-GP-anti-(R-IgG) need by prepared. For best results in terms of accuracy, a supply of highly purified antibody must be available for making the solid phase antibody specific to the antigen being tested, or a supply of specific solid-phase antibodies must be maintained. In addition, a highly purified supply of the antibody of the second species to the antigen must be maintained. Of course, use of $^{125}I$ as a labeling radionuclide has all of the attendant problems noted above.

While the conjugate produced by Pritchard et al was a useful first step, it did not provide a basis for successful practice nor produce a general method utilizing multiple antibody moieties.

Another approach involves the formation of an antigen-antibody complex linked to an enzyme. The development of enzyme-linked immunoadsorbent assays (ELISA) has been made possible by current developments in protein conjugation techniques. Prior workers have found that the bifunctional reagent of choice for coupling enzyme labels to protein in the ELISA methods is almost exclusively glutaraldehyde. The conjugates prepared with glutaraldehyde have been reported to retain immunologic and enzymatic activity much better than those obtained with a carbodiimide coupling reagent. However, glutaraldehyde reactions with proteins have been reported to produce different degrees of crosslinkage depending on the conditions. For example, protein polymers of low molecular weight are reported to be produced at low protein concentrations, while higher protein concentrations yield water-insoluble polymers of excellent immunadsorbent capacity. A major problem of the prior art has been to retain the antigenic activity of the conjugate. Thus, for example, alkaline phosphatase-rabbit IgG conjugates, conjugated with glutaraldehyde, which contain 40% of the total protein after the coupling reaction, have been reported to produce a high degree of sensitivity in enzyme-linked immunadsorbent assays. While enzymatic activity is well preserved following such a conjugation, antigenic activity of the IgG moiety has been found to be very low, though delayed addition of the IgG to the alkaline phosphatase-glutaraldehyde reaction mixture has been reported to decrease this loss of immunological activity somewhat.

The problems enumerated in the foregoing are not intended to be exhaustive, but rather, are among many which tend to impair the effectiveness of previously suggested terminal radionuclide labeling or chelate-short lived radionuclide labeling techniques. Other noteworthy problems may also exist; however, those presented above should be sufficient to demonstrate that terminal labeling ratioimmunoassaying techniques of the prior art have not been entirely successful.

Recognizing the need for an improved terminal labeling radioimmunoassaying technique and method and an improved method for synthesizing a chelate-conjugate for use therein, it is therefore, a general feature of the present invention to provide a novel terminal labeling radioimmunoassaying method and method of synthesizing chelate-conjugates for use therein which minimizes or reduces the problems of the type previously noted.

It is a more particular feature of the present invention to provide a universal reagent having a chelating moiety for subsequent binding with a short-lived radionuclide for radioimmunoassay.

It is yet another feature of the present invention to provide a method for synthesizing an improved conjugate having a coupling moiety of a component capable of binding with specific metal ions for use in the radioimmunoassaying technique of the present invention.

Specifically, the present invention comprises an improvement to prior methods in which a "universal" antibody has been used. In accordance herewith the universal antibody is formed with a component, e.g., a chelating protein such as, e.g., transferrin, desferoxamine, or the like capable of binding a radionuclide. The second complex is reacted with a radionuclide and the radioactivity of the bound radionuclide is measured.

More specifically, the present invention relates to an immunoradiometric assaying method employing terminal labeling with a radionuclide having a relatively short half-life through the use of a chelating moiety on the protein desired to be labeled, to which the radionuclide attaches allowing measurement of the amount of the labeled protein, e.g., an antibody or antigen-antibody complex. An unknown quantity of an antigen, for example, is reacted with an insoluble antibody specific to the antigen and of a first species and the complex thus formed reacted with a second antibody specific to the antigen and of the second species. The complex thus formed is reacted with a third antibody of a species different from the second antibody and containing a chelating moiety. A suitable radionuclide having a short half-life, e.g., In-133m (which is a metastable state of Indium 113 which decays to ground level of Indium 113 by gamma emission) is then added to the complex thus formed and attaches to, i.e., "labels" the complex thus formed for purpose of radioimmunoassay.

DETAILED DESCRIPTION

Figure 1:
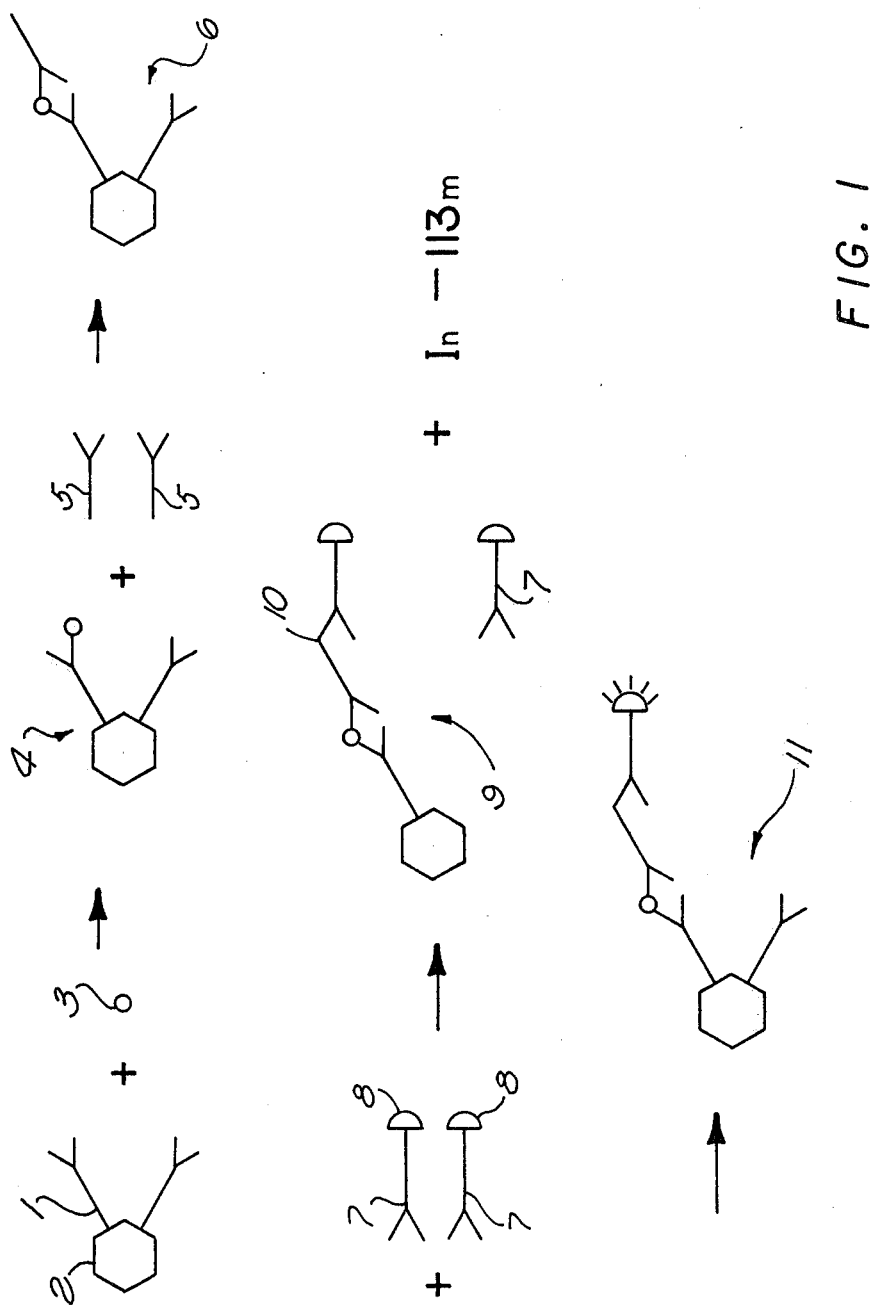
FIG. 1 shows a schematic drawing of the radioimmunoassay method of the present invention.

In a preferred embodiment of the present invention we provide an improved method of complexing Indium-113m to a transferrin moiety coupled with an antibody for use in the improved terminal labeling method employing a truly universal reagent and a short-lived radionuclide for the terminal labeling.

The present invention proceeds by several general steps: conjugation of a universal antibody with a chelating moiety such as transferrin, desferoxamine or the like; terminal labelling of the antigen-antibody complex with the conjugated universal antibody and binding of radioactive nuclide to the chelating moiety; and measurement of radioactivity of the complex. However, it will lend more clarity to first consider the problem of binding of a radioactive nuclide to the chelating moiety, exemplified by transferrin. A number of ions, e.g., indium and gallium or the like are suitable for use in the present invention because they have radionuclides of relatively short half-life in comparison to I-125. In-113m was selected as the preferred embodiment because of its short half-life of 1.67 hours and its ready availability from a long lived Sn-113 generator, that is commercially available, such as has been produced by the New England Nuclear Co.

Binding of In-113 to Transferrin

A method according to the present invention achieves rapid and reproducible binding of radioactive indium to a transferrin moiety at an approximately neutral pH of 7.4, achieving 83% binding. Nitrilotriacetic acid (NTA) is used as an intermediate carrier ligand, whose function is to maintain the In-113 ion in solution in Tris buffer (2-amino-2-hydroxy methyl-1,3 propanediol), with a pH of 7.4, so that it can thenbe transferred rapidly to specific binding sites on the transferrin. Complexation is facilitated by the presence of a synergistic ion such as bicarbonate.

Transferrin has a molecular weight of approximately 77,000 and contains two specific metal-binding sites per molecule. The two metal binding sites are not structurally identical but they bind iron independently of each other. The two stability constants for the indium-transferrin complex ($K_1 = 10^{31}$, $K_2 = 10^{27}$) appear to be of the same order of magnitude as for iron-transferrin complex. Physiologically, only 30% of the total serum transferrin is saturated with iron. When iron concentrations in the blood are below this level of saturation, iron is bound exclusively to the transferrin, and when they exceed this level the excess iron is distributed among various serum proteins in a manner as yet not clarified in the art. Thus, use of transferrin in an indirect terminal antibody labeling method is dependent upon the indium binding capacity of the actual assay system. Further, indium salts hydrolyze and produce insoluble hydroxide at pH values higher than 3, highlighting the significance of selected aspects of indium chemistry crucial to the method of the present invention.

In-113 is eluted from the generator using a solvent of high acidity, e.g., 0.05 N HCl. The dominant state of indium in aqueous solution at pH 3 or less is the hydrated form with six water molecules $[In(H_2O)_6^{+3}]$. Above pH 3.4, indium tends to precipitate as the hydroxide $[In(OH)_3]$ and at high hydroxide concentrations the precipitate is "peptidized" to a colloidal state. The use of weak chelating agents provides a practical solution to avoiding hydroxide precipitation at the neutral pH ranges required for specific binding of indium ions to chelators such as transferrin, or desferoxamine or the like. A suitable transition chelator must have the properties of competitive rates of formation against hydroxide precipitation and stability constants still favorable for the formation of the final indium-transferrin complex.

Nitrilotriacetic acid has been suggested by the art to be an intermediate chelator for iron characterized by fast transfer of the metal to the transferrin. It has been shown that the iron exchanges from a nitrilotriacetic acid complex to transferrin rapidly (less than 10 seconds) and yields a linear response curve with a clear end point. This is contrary to most other iron complexes and probably due to the monomeric nature of the nitrilotriacetic acid-iron complex.

It was found that NTA was unable to prevent precipitation of indium in Tris buffer, pH 7.4, at NTA/indium ratios of 1:1 to 100:1. Tris buffer was chosen to avoid the potential formation of insoluble indium phosphates with the use of phosphate buffers. As in the case of iron-transferrin complexing a synergistic anion was determined to be required as a transport mechanism to facilitate the indium transferrin complexing. The specific binding of iron to transferrin was known to require such a synergistic anion for each binding site since the metal binding sites have virtually no affinity for iron in the absence of bicarbonate or other synergistic anion.

It was thus determined that the metal ion sequestering species consists of the apotransferrin-bicarbonate binary complex. Under physiological conditions unsaturated transferrin exists almost entirely in this form. The postulation that bicarbonate and metal binding sites are interlocking and that the bicarbonate acts as a ligand for the transferrin-indium complex in the same fashion as for iron was experimentally tested and verified. Acidic indium chloride solutions were added to rabbit serum ultra-filtrate, which showed, through quantitative binding yield observed, that the ionic environment of the serum was, by itself, incapable of maintaining indium ions in solution. However, Indium-113m tagging to transferrin was found, through electrophoretic studies, to have occurred to a significant extent in the serum ultrafiltrate to which transferrin had been added. Thus, the synergistic anion, or counter ion, such as bicarbonate appears to be necessary to achieve good complexation of indium to transferrin.

The following example illustrates a method for binding indium to transferrin according to the present invention.

EXAMPLE 1

Iron-free human transferrin and nitrilotriacetic acid were obtained from Sigma Chemical Company. Indium-113m was eluted from a Sn-113 generator as a chloride in 0.5 N HCl. All other chemicals used were of reagent grade.

The Sn-113 generator was eluted at 24 hour intervals to achieve a constant yield of indium and to maintain a constant carrier concentration in solution.

The transferrin was dialyzed for 24 hours at 4° C. against 0.05 M Tris buffer at pH 7.4 before use in the method of the present invention.

Rabbit serum ultrafiltrate was prepared using Amicon "Centriflo" membrane cones CF 25.

The eluting solvent for In-113 from the Sn-113 generator consisted of 0.05 N HCl. Since at increased pH values indium salts hydrolyze to insoluble hydroxide, the minimum HCl concentrations necessary to maintain indium chloride in solution was required to be determined prior to conducting solubility studies of indium ions in various buffer solutions. In order to accomplish this 60 micro-Ci of In-113m chloride contained in 100 micro-liters 0.05 N HCl was added to test tubes containing 10 ml of each of the HCl solutions in order to yield final HCl concentrations between 0.5 and $50 \times 10^{-3}$ N. Each tube was then centrifuged at 4000 rpm for 10 minutes. The activity in the precipitates and in 100 micro-liters of the supernatant solution from each tube was counted. Indium hydroxide precipitate was not observed until dilution reached a concentration of 2.5 $10^{-3}$ N HCl. Significant precipitation of the In-113 was evident at concentrations lower than $10^{-4}$ N.

NTA was used as an intermediate chelator with bicarbonate as the counter ion. 24 micro-Ci of In-113-NTA complex at a 4:1 NTA/indium ratio in a 40 microliter 0.05 N HCl solution was added to 2 ml 0.05 M Tris buffer (pH 7.4) containing 5 mM bicarbonate. By applying these samples to Corning special purpose agarose film and using electrophoresis in sodium barbital buffer, pH 8.6, with a 2 mA current applied to each film strip for 30 minutes at 4° C., the in vitro transferrin labeling efficiency with indium was determined to be 81% as against an 83% for a rabbit serum ultrafiltrate reference solution.

Without transferrin the In-113 radioactivity did not bind to any specific fraction, and without the counter ion bicarbonate the In-113 did not bind at all.

Conjugation with Chelating moiety

Conjugation of the antibody (the IgG fraction of goat anti-rabbit-IgG) with transferrin, desferoxamine or the like is accomplished using glutaraldehyde as a coupling agent. Optimization of total protein concentration and glutaraldehyde levels was accomplished to obtain end products where the specific metal binding capacity of the transferrin moiety remains unchanged and the antibody retains at least 70% of its antigenic activity. In contrast, prior art conjugation labeling techniques designed to avoid the damage caused to the antibody by direct iodination of the protein molecules have conjugation occurring at the tyrosyl groups, thus reducing antibody titer.

One aspect of the present invention relates to the glutaraldehyde coupling reaction for preparing antibody-heavy metal chelate conjugates, e.g., IgG-transferrin and IgG-desferoxamine. The heterogeneity of such conjugates was assayed electrophoretically on agarose gel, suggesting the presence of soluble polymers of various size, composition, and possibly varying potencies as the labeled antibody reagent. It was determined that the principal factors affecting the conjugate coupling reaction were pH, IgG/chelate (e.g., transferrin, desferoxamine, or the like) ratio, total protein concentration and glutaraldehyde concentration. It was found that insolubilization of the conjugate was increased as the protein concentration or the glutaraldehyde concentrations were increased. However, low glutaraldehyde concentrations were found to be required for reduction in antibody damage. The following examples illustrate the conjugation method of the present invention.

EXAMPLE 2

IgG-transferrin conjugation

At a working volume of one ml, 4 mg. iron-free transferrin was mixed with 2-8 mg IgG fraction of goat antirabbit IgG in 0.01 M phosphate buffer (pH 6.8-7.4). To this mixture containing a final total protein concentration of 6-12 mg/ml and an IgG/transferrin mole ratio of 1:1 to 1:4, 100 micro-liters of freshly prepared 0.5-1% glutaraldehyde solution was added. The coupling reaction was carried out for two hours at room temperature, followed by dialysis overnight at 4° C. against metal-free phosphate buffered saline (pH 7.4). The dialysis sac containing the conjugate was transferred to a container holding metal-free 0.05 M Tris buffer (pH 8.0) and dialyzed for 24 hours at 4° C. The conjugate was then centrifuged at 2000 rpm for 20 minutes for removal of any insoluble products. Bovine serum albumin was added at a final concentration of 1% for stabilization and the conjugate was stored at 4° C. with 0.02% sodium azide added as a preservative.

EXAMPLE 3

IgG-desferoxamine conjugate

The conjugation was carried out using the same procedure as in Example 1. The reaction mixture contained 1–8 mg IgG fraction of goat antirabbit IgG at an IgG-/desferoxamine mole ration 1:1 to 1:10. Freshly prepared 0.5% glutaraldehyde solution was added to achieve a final glutaraldehyde concentration of 0.025–0.05%.

The immunoreactivity of the IgG fraction of goat antirabbit IgG was tested against rabbit IgG and normal rabbit sera on Ouchterlony immunodiffusion plates before and after the glutaraldehyde coupling reaction to determine the retention of antibody activity in each of the conjugates. The retention in transferrin immunoreactivity was also determined against goat antihuman transferrin to confirm its structural integrity after the conjugation. The electrophoretic mobilities of IgG-transferrin and IgG-desferoxamine conjugates were determined on agarose gel. All conjugates were found to possess higher electrophoretic mobilities than their respective components. A continuous pattern of a range of electrophoretic mobilities were observed, rather than the distinct electrophoretic bands shown by the parent protein. These results suggest the heterogeneous nature of the conjugate populations. The labeling efficiency of the conjugates were determined by radioelectrophoresis. Indium-113m-nitrilotriacetic acid complex was added to the conjugate preparations of Examples 2 and 3 at a ratio of 1:10 by volume, containing bicarbonate as the synergistic anion. The working range of indium concentration was kept below the saturation level of transferrin in the samples. Over 80% of the activity was observed to be concentrated in the conjugate region.

The integrity of the conjugate was tested by direct comparison to an unconjugated mixture of IgG fraction of goat antirabbit IgG and transferrin. Independent behavior of the unconjugated mixture components to form two distinct precipitin lines on immunodiffusion plates against goat antihuman transferrin and rabbit IgG was modified with the conjugation to render the formation of a single precipitin line.

The IgG-desferoxamine conjugate prepared using an IgG/desferoxamine mole ratio of 1:1 at an IgG concentration of 4 mg/ml and a final glutaraldehyde concentration of 0.025% was observed to retain 70% of its immunoreactivity. Extensive precipitation was observed at an IgG concentration of 8 mg/ml and glutaraldehyde concentration of 0.05%.

Terminal labeling

The conjugation according to the present invention provides the means for terminal labeling for radioimmunoassay, e.g., double antibody immunoradiometric assay (i.e., 2-site IRMA). Radiometal labeling by means of a covalently bound chelating agent to a protein molecule using indium ions with, e.g., transferrin, according to the present invention eliminates the "decay catastrophe" effects and other undesirable side effects of direct labeling, e.g., with radioactive iodine prelabeled reagents.

A 2-site or sandwich technique is used according to the present invention to enhance specificity by utilizing two separate sites on the antigen molecule for binding. The indirect labeling technique of the present invention using an anti-antibody conjugate results in applicability to numerous polypeptide assays as a universal reagent thus limiting waste of specific antisera during conjugation. Use of an unmodified specific antibody in the first reaction of the 2-site IRMA method, comprising one example of the present invention, further enhances the specificity of the method of the present invention. Amplification of the specific activity of the assay method is also resultant from the ability of the specific antibody to react with 2 to 3 molecules of the second antibody (the universal reagent.)

The following example illustrates the terminal labeling technique of the present invention includes using an anti-IgG-transferrin conjugate prepared as described in Example 2.

EXAMPLE 4

An IgG fraction of goat-anti-rabbit IgG was obtained from Miles Laboratories, Iron-free human transferrin was obtained from Sigma Chemical Co., and Phadebas hGH Prist reagents were obtained from Pharmacia Diagnostics. Indium-113m chloride was eluted from a Sn-113 generator at 24 hour intervals to keep indium yield in solution a constant concentrations. All other chemicals used, e.g., in preparing buffering solutions were of reagent grade.

Standard solutions of hGH containing 0.05–15 micro-units/100 micro-liters were incubated with sheep anti-hGH (S-anti-hGH) coupled paper discs for 3 hours at room temperature and the solid phase then washed 3 times with a 2.5 ml isotonic (0.9%) saline. 8 micro-grams/100 micro-liters of rabbit anti-hGH (R-anti-hGH) was then added and the mixture was incubated overnight at room temperature. Excess soluble R-anti-hGH was then washed off 3 times as described above and 50 micro-liters of goat-antirabbit-IgG-transferrin conjugate (G-anti-R-IgG-transferrin), prepared in accordance with Example 2 was added. This mixture was incubated for 72 hours at 4° C.

The solid phase fixed conjugate and the soluble conjugate contained in this incubated mixture were then labeled by adding an In-113m-NTA complex prepared in accordance with Example 1 at 0.25% transferrin saturation level. After 20 minutes, the unbound conjugate was washed off from the solid phase fixed conjugate with a 0.005 M Tris buffer, pH 7.4 and the radioactivity of the solid phase was determined.

Separation of the bound conjugate from the free fraction following the labeling step insures a constant working level of transferrin concentration for all assay samples. Through the use of this postlabeling separation technique activity differences at the solid phase resulting from differing sample concentrations of antigen being measured still operates even at low transferrin saturation levels, (i.e., on the order of 0.25%). Specific activity is amplified through the use of higher transferrin saturation levels.

In this manner a standard curve is obtained by varying the initial hGH concentrations in the standard solutions used. Thus unknown concentrations of antigen being tested can be compared with the standard curve derived and the concentration in the unknown amount of the tested antigen determined.

Turning now to FIG. 1, a schematic view of the immunoradiometric assay technique of the present invention is shown.

S-anti-hGH antibody 1 is shown schematically to be in solid phase coupled to, e.g., a paper disc shown schematically at 2. Into the container having this solid phase coupled antibody 1 is added a solution containing an unknown amount of antigen 3 specific to the solid phase antibody 1, in the examples of the present invention, hGH.

The antibody and antigen complex, leaving S-anti-hGH-hGH complex 4 in solid phase coupled to the, e.g., paper disc 2. After washing, an antibody from a different species, but specific to the antigen being tested, e.g., R-anti-hGH 5 is then added resulting in a S-anti-hGH-hGH-R-anti hGH complex 6 in solid phase coupled to the paper disc 2. Washing again occurs to remove the unreacted R-anti-hGH 5.

An antibody from yet another species is then used which also has a tranferrin or other chelating moiety conjugated to it. In the example of the present invention this conjugate comprises goat anti-R-IgG transferrin conjugate 7 (G-anti-R-IgG-transferrin) with the transferrin moiety indicated at 8. This is added and reacted with the complex in the solid phase resulting in a S-anti-hGH-hGH-R-anti-hGH-G-anti-R-IgG-transferrin complex 9 coupled to paper disc 2, and an excess amount of G-anti-R-IgG-transferrin complex 7 left in solution. Since this antibody reacts with the "back" of the R-anti-hGH at 10 it does not need to be specific to hGH and thus is a truly universal reagent for the first species.

Indium-113m is then added and attaches to the transferrin moiety on both the solid phase (as shown at 11) and soluble unreacted conjugates. When the unreacted soluble G-anti-R-IgG-transferrin conjugate is then separated from the solid phase coupled to paper disc 2, the measure of radioactivity from the complex 11, now tagged with indium, is a measure of the concentration of the original sample of antigen 3.

The use of the NTA-indium complex as a labeling reagent in the present invention with the presence of synergistic bicarbonate ions appears to mask the non-specific metal binding sites of the other proteins in the assay system. The affinity of the indium ions for the solid phase antibody was less than 1%, with indium-transferrin complexing appearing to be the dominant reaction at the working indium concentrations employed.

As an alternative to the successive incubation of the anti-hgH and anti-hgH-transferrin conjugate, a precombined IgG-anti-IgG-transferrin complex can be prepared to eliminate the incubation steps in the clinical laboratory during the immunoradiometric assaying technique of the present invention.

The terminal labeling technique of the present invention is also adaptable to monovalent immunoradiometric assay and competitive protein binding assay and RIA systems, and not limited to the 2-site immunoradiometric assay model described in the example above.

The foregoing description of the invention has been directed to a particular preferred embodiment and for purposes of explanation and illustration. It will be apparent, however, to those skilled in the art that many modifications and changes in the methods and materials may be made without departure from the scope and spirit of the invention. For example other chelating agents, and other coupling techniques, may be used. Particular radionuclides described have been chosen for convenience and are not preclusive. It is the Applicants' intention in the following claims to cover all such equivalent modifications and variations as fall within the true spirit and scope of the invention.

We claim:

1. In a method of immunoradiometric assay in which (a) an antigen and (b) an antibody specific to said antigen, are reacted to form a first complex which is reacted with a universal antibody for said complex from a species different from that of said specific antibody to form a second complex, and said second complex is separated from unreacted universal antibody and measured, the improvement according to which said universal antibody comprises a component capable of binding a radionuclide and including the steps of reacting a radionuclide with said separated second complex to bind said radionuclide to said universal antibody and measuring the radioactivity of said bound radionuclide.

2. The method of claim 1 wherein said universal antibody is of a species different from said antigen and said specific antibody.

3. The method of claim 1 wherein said component is a chelating agent.

4. The method of claim 3 wherein said chelating agent is of the group including transferrin, desferoxamine and D-penicillamine.

5. The method of claims 2, 3 or 4 wherein said radionuclide is a radionuclide having a relatively short half-life.

6. The method of claim 2, 3 or 4 wherein said radionuclide is Indium-113.

7. The method of claim 1 wherein said component is transferrin.

8. The method of claim 7 wherein said radionuclide is a radionuclide having a relatively short half-life.

9. The method of claim 7 wherein said radionuclide is Indium-113.

10. In a method for complexing a radionuclide to a conjugate containing a component capable of binding a radionuclide comprising the steps of combining the chelate in a buffered solution with a salt of the radionuclide in the presence of nitriloacetic acid and a synergistic anion, the improvement comprising preparing said buffered solution using an eluting solvent for the radionuclide having an acid concentration sufficiently low to maintain said salt in solution.

11. The method of claim 10 wherein the component is a chelating agent.

12. The method of claim 11 wherein said chelating agent is of the group including transferrin, desferoxamine and D-penicillamine.

13. The method of claim 10 wherein the component is transferrin.

14. The method of claims 10, 11 or 12 wherein said radionuclide is a radionuclide having a relatively short half-life.

15. The method of claims 10, 11 or 12 wherein the radionuclide is Indium-113.

16. A method of terminal labeling for radioimmunoassay comprising the steps of:
 adding an unknown quantity of an antigen to an insoluble first antibody, from a first specie, specific to said antigen, and allowing all of said antigen to react with said first antibody to form a reacted amount of a first complex;
 adding a second antibody from a second specie, specific to said antigen, and allowing said second antibody to react with said reacted amount of said first complex to form a reacted amount of a second complex and an excess unreacted amount of said second antibody;

removing said excess unreacted amount of said second antibody;

adding a third antibody from a specie different from said second specie, to said reacted amount of said second complex, said antibody being conjugated with a chelating moiety from the group including transferrin, desferoxamine and D-penicillamine said third antibody reacting with said reacted amount of said second complex to form a reacted amount of a third complex and an excess unreacted amount of said third antibody;

adding a radionuclide which will attach to said chelating moiety on said third complex and said third antibody;

removing said excess unreacted amount of said third antibody; and measuring the radioactivity in said reacted amount of said third complex.

17. The method of claim 16 wherein said third antibody is of a species different from said second antibody and said first antibody.

18. The method of claim 16 wherein said radionuclide is short lived.

19. The method of claim 18 wherein said radionuclide has a half-life of less than 24 hours.

20. A method of terminal labeling for radioimmunoassays comprising the steps of:

adding an unknown quantity of an antigen to an insoluble first antibody, from a first species, specific to said antigen and allowing all of said antigen to react with said first antibody to form a reacted amount of a first complex;

adding a second antibody from a second species, specific to said antigen, and allowing said second antibody to react with said first complex to form a reacted amount of a second complex and an excess unreacted amount of said second antibody;

removing said excess unreacted amount of said second antibody;

adding a third antibody, of a specie different from said second antibody, to said reacted amount of said second complex, said third antibody being conjugated with a chelating moiety from the group including transferrin, desferoxamine and D-penicillamine, said third antibody reacting with said reacted amount of said second complex to form a reacted amount of a third complex and an excess unreacted amount of said third antibody;

adding Indium-113m which will attach to said chelating moiety in said reacted amount of said third complex and said excess unreacted amount of said third antibody;

removing said excess unreacted amount of said third antibody; and, measuring the radioactivity in said reacted amount of said third complex.

21. A method of terminal labeling for radioimmunoassays comprising the steps of:

adding an unknown quantity of an antigen to an insoluble first antibody, from a first species, specific to said antigen and allowing all of said antigen to react with said first antibody to form a reacted amount of a first complex;

adding a second antibody from a second species, specific to said antigen, and allowing said second antibody to react with said first complex to form a reacted amount of a second complex and an excess unreacted amount of said second antibody;

removing said excess unreacted amount of said second antibody;

adding a third antibody, of a species different from said second antibody, to said reacted amount of said second complex, said third antibody being conjugated with a transferrin moiety, said third antibody reacting with said reacted amount of said second complex to form a reacted amount of a third complex and an excess unreacted amount of said third antibody;

adding Indium-113m which will attach to said transferrin moiety in said reacted amount of said third complex and said excess unreacted amount of said third antibody;

removing said excess unreacted amount of said of said third antibody; and measuring the radioactivity in said reacted amount of said third complex.

* * * * *

UNITED STATES PATENT AND TRADEMARK OFFICE
CERTIFICATE OF CORRECTION

PATENT NO. : 4,320,109

DATED : March 16, 1982

INVENTOR(S) : Robert Nakamura et al

It is certified that error appears in the above-identified patent and that said Letters Patent is hereby corrected as shown below:

Column 5, line 1, "ratioimmunoassaying" should read -- radioimmunoassaying --.

Column 10, line 26, "a constant" should read -- at constant --.

Signed and Sealed this

Third Day of August 1982

[SEAL]

Attest:

GERALD J. MOSSINGHOFF

Attesting Officer     Commissioner of Patents and Trademarks